United States Patent
Toomey et al.

(10) Patent No.: US 10,299,769 B2
(45) Date of Patent: May 28, 2019

(54) FLEXIBLE BIOPSY NEEDLE

(71) Applicant: Cook Medical Technologies LLC, Bloomington, IN (US)

(72) Inventors: Ciaran Toomey, Rathcormac (IE); Darach McGrath, Nenagh (IE); Michael Clancy, Limerick (IE); Triona Campbell, County Clare (IE)

(73) Assignee: Cook Medical Technologies LLC, Bloomington, IN (US)

( * ) Notice: Subject to any disclaimer, the term of this patent is extended or adjusted under 35 U.S.C. 154(b) by 78 days.

(21) Appl. No.: 14/729,860

(22) Filed: Jun. 3, 2015

(65) Prior Publication Data

US 2015/0265258 A1 Sep. 24, 2015

Related U.S. Application Data

(63) Continuation of application No. 13/526,968, filed on Jun. 19, 2012, now abandoned.
(Continued)

(51) Int. Cl.
*A61B 10/04* (2006.01)
*A61B 10/02* (2006.01)
(Continued)

(52) U.S. Cl.
CPC .............. *A61B 10/04* (2013.01); *A61B 1/018* (2013.01); *A61B 1/2733* (2013.01);
(Continued)

(58) Field of Classification Search
None
See application file for complete search history.

(56) References Cited

U.S. PATENT DOCUMENTS 4,331,130 A * 5/1982 Lewicky ............. A61F 9/00736
604/23
4,350,169 A 9/1982 Dutcher et al.
(Continued)

FOREIGN PATENT DOCUMENTS

DE   10 2004 056 136 A1   5/2006
WO   WO 2006/065913 A1   6/2006
(Continued)

OTHER PUBLICATIONS

Machine Translation of DE 102004056136, 5 pages, printed out on Sep. 16, 2014.*
(Continued)

*Primary Examiner* — Matthew Kremer
(74) *Attorney, Agent, or Firm* — Brinks Gilson & Lione

(57) ABSTRACT

An endoscopic tissue-sampling needle includes an elongate needle shaft having a proximal and a distal shaft portion. The proximal shaft portion includes an inner tubular core that may be constructed of a same material as the distal shaft portion, having a longer length and a smaller outer diameter than the distal shaft portion. The distal shaft portion extends into and is fixedly attached to an inner diameter of a distal shaft portion lumen. The distal shaft portion lumen is configured for collection of patient tissue, with a distal penetrating tip and/or a side aperture with a cutting edge configured to excise tissue from a target site in a patient body. The proximal shaft portion includes polymer coating around the inner tubular core, which is configured to provide an outer diameter for the proximal shaft portion that may be substantially the same as the outer diameter of the distal shaft portion.

12 Claims, 8 Drawing Sheets

Related U.S. Application Data

(60) Provisional application No. 61/502,086, filed on Jun. 28, 2011.

(51) Int. Cl.
    *A61B 1/018*     (2006.01)
    *A61B 1/273*     (2006.01)
    *A61B 8/08*     (2006.01)
    *A61B 17/3205*     (2006.01)
    *A61B 10/00*     (2006.01)
    *A61B 17/00*     (2006.01)
    *A61B 17/34*     (2006.01)

(52) U.S. Cl.
    CPC ............ *A61B 1/2736* (2013.01); *A61B 8/481* (2013.01); *A61B 10/0275* (2013.01); *A61B 10/0283* (2013.01); *A61B 17/32053* (2013.01); *A61B 17/3496* (2013.01); *A61B 2010/0093* (2013.01); *A61B 2010/045* (2013.01); *A61B 2017/0034* (2013.01); *A61B 2017/3413* (2013.01)

(56) References Cited

U.S. PATENT DOCUMENTS

| | | | | |
|---|---|---|---|---|
| 4,781,691 | A * | 11/1988 | Gross | A61B 17/3401 604/164.06 |
| 5,061,238 | A | 10/1991 | Schuler | |
| 5,168,864 | A * | 12/1992 | Shockey | A61B 1/0057 600/131 |
| 5,490,521 | A * | 2/1996 | Davis | A61B 8/0833 600/458 |
| 5,836,914 | A * | 11/1998 | Houghton | A61B 17/3401 604/117 |
| 6,129,750 | A | 10/2000 | Tockman et al. | |
| 6,203,524 | B1 | 3/2001 | Burney et al. | |
| 2002/0022788 | A1 | 2/2002 | Corvi et al. | |
| 2004/0068256 | A1 * | 4/2004 | Rizoiu | A61B 18/20 606/13 |
| 2004/0260199 | A1 | 12/2004 | Hardie, Jr. et al. | |
| 2009/0177114 | A1 | 7/2009 | Chin et al. | |
| 2010/0081965 | A1 | 4/2010 | Mugan et al. | |
| 2010/0114031 | A1 * | 5/2010 | Jarial | A61B 10/0275 604/164.11 |
| 2010/0298736 | A1 | 11/2010 | Levy | |
| 2011/0137412 | A1 * | 6/2011 | Nyte | A61F 2/12 623/8 |

FOREIGN PATENT DOCUMENTS

WO    WO 2008/098241 A1    8/2008
WO    WO 2011/053648 A1    5/2011

OTHER PUBLICATIONS

Cook Medical, "Variable Injection Needle" 2010, 8 pgs.
Cook Medical, "Variable Injection Needle", IFU for Cook DVI (disposable varices injector) needle, 2010, 41 pgs.
PCT International Search Report and Written Opinion for PCT Application No. PCT/US2012/042903, dated Aug. 27, 2012.
Robbins Instruments Inc., "Titanium Nitride Scalp Transplant Punches", robbinsinstrument.com, Jul. 15, 2010, 2 pgs.

* cited by examiner

FLEXIBLE BIOPSY NEEDLE

CROSS-REFERENCE TO RELATED APPLICATIONS

This application claims priority under 35 USC § 119 to U.S. Provisional Application Ser. No. 61/502,086, filed Jun. 28, 2011, and under 35 USC § 120 as a continuation of U.S. application Ser. No. 13/526,968, filed Jun. 19, 2012, each of which is incorporated herein by reference in its entirety.

TECHNICAL FIELD

The invention relates generally to medical needles. More particularly, the invention pertains to medical needles configured for ultrasound-guided endoscopic biopsy.

BACKGROUND

Endoscopists have developed great expertise in using elongate needles, including echogenic needles viewable under ultrasound, to obtain samples from patients in a minimally invasive manner. In particular, they use devices and techniques that allow carefully targeted collection of samples from deep in patient bodies without any external percutaneous incisions or punctures. Devices such as fine needle aspiration needles and fine needle biopsy needles may be directed through a working channel of an endoscope (e.g., duodenoscope, gastrointestinal end-viewing endoscope) to a target site in a patient body.

In order to obtain useful samples of tissue suitable for histological and/or cytological analysis, it is desirable to use a large-gauge needle. However, these needles are often considered stiff and unwieldy by some users who find them difficult to insert fully into, for example, a working channel of an endoscopic ultrasound (EUS) endoscope. In addition, as these needles typically include an outer sheath, it may be difficult to advance the penetrating/collecting distal end portion through and out of the sheath. These challenges may be particularly problematic when a user is attempting to access more difficult-to-reach anatomical locations (such as, for example, attempting to access the head of a patient's pancreas from the duodenum).

It would therefore be advantageous to provide a needle that includes a distal end dimensioned to collect samples of a desirable size while also providing a shaft proximal of that distal end that obviates the present difficulties of advancement and navigation through an endoscope working channel and through patient anatomy. The shaft provided should still provide desirable pushability and trackability so that the needle will be navigable in a manner consistent with the desires and aims of users to accurately obtain samples.

BRIEF SUMMARY

In one aspect, an endoscopic tissue-sampling needle may be provided including an elongate needle shaft having a proximal shaft portion and a distal shaft portion. The proximal shaft portion includes a tubular body that includes a polymeric material while the distal shaft portion is constructed from a metallic material. The distal shaft portion may extend into and be fixedly attached to an inner diameter of a proximal shaft portion lumen. The distal shaft portion lumen preferably is configured for collection of patient tissue by including a distal penetrating tip and/or a side aperture with a cutting edge configured to excise tissue from a target site in a patient body. The proximal shaft portion may include a proximal metallic shaft portion with an intermediate polymeric portion between it and the distal shaft portion.

BRIEF DESCRIPTION OF THE DRAWINGS

FIG. 6 shows a needle embodiment including a proximal metal portion, an intermediate polymeric portion, and a distal metal portion, while

DETAILED DESCRIPTION

Figure 1:
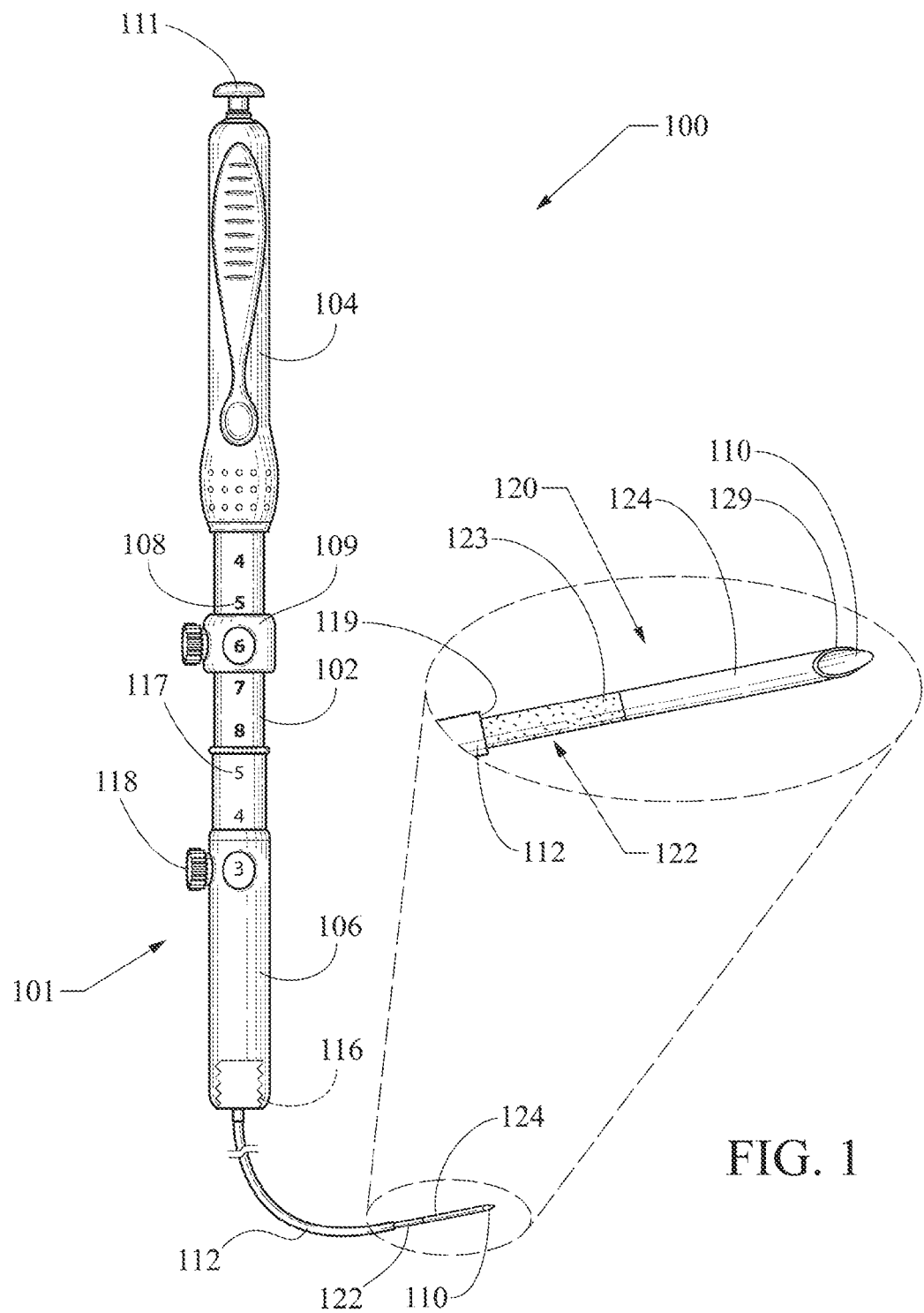
FIG. 1 shows a needle device embodiment with a detail of a distal region thereof.

Embodiments are described with reference to the drawings in which like elements are generally referred to by like numerals. The relationship and functioning of the various elements of the embodiments may better be understood by reference to the following detailed description. However, embodiments are not limited to those illustrated in the drawings, and features of various embodiments—whether described in text and/or in drawing figures—may be incorporated into other embodiments within the scope of the present invention. It should be understood that the drawings are not necessarily to scale, and in certain instances details may have been omitted that are not necessary for an understanding of embodiments of the present invention, such as—for example—conventional fabrication and assembly.

As used in the specification, the terms "proximal" and "distal" should be understood as being in the terms of a physician or other person operating a medical device or on a patient. Hence, the term "distal means the direction or portion of the device that is farthest from the physician or other person and the term "proximal" means the portion of the device that is nearest to the physician or other person.

An endoscopic biopsy needle device 100, which may be scaled and configured for use in fine-needle aspiration (FNA) and/or fine-needle biopsy (FNB) procedures, or other tissue-collection procedures, is described with reference to FIG. 1. The needle device 100 is shown here with a handle 101. The handle 101 includes a sheath-attached handle member 102 with a needle-attached handle member 104 longitudinally slidably disposed on its proximal end. A scope-attachment handle member 106 is slidably attached to the distal end of the sheath-attached handle member 102. The sheath-attached handle member 102 is attached to the needle sheath 112 and the needle-attached handle member 104 is attached to the needle 120 (which may be configured in the manner of any of the needles disclosed herein or later developed in accordance with principles of the present disclosure). The sheath 112 may be constructed as a protective sheath configured to cover the needle 120 while it is being advanced through an endoscope working channel, which sheath will protect both the needle and the working channel from contact that could damage either or both.

The scope-attachment handle member 106 may be configured for incrementally-fixable, longitudinally-adjustable (relative to the other handle components) attachment to the exterior of a working channel of an endoscope such as—for example—an end-viewing gastric endoscope, duodenoscope, or EUS endoscope (not shown) using, for example, a threaded cavity 116. The scope-attachment handle member 106 allows a user to determine the distance by which the sheath 112 will extend from a standard-length endoscope, and it may include numerical indicia 117 corresponding to that relative length and an adjustable engagement structure 118 allowing a user to select a length and engage the scope-attachment handle member 106 accordingly.

The sheath-attached handle member 102 includes numerical indicia 108 and an adjustable ring 109 that limits the movement of the needle-attached handle member 104 and provides a way to select the distance to which the needle 120 may be extended beyond the sheath 112. By way of illustration, the configuration shown in FIG. 1 would allow the sheath to extend 3 units (e.g., inches, cm) beyond the distal end opening of an endoscope working channel, and the needle 120 would be allowed to extend up to 6 units beyond the distal end of the sheath 112, although its current position would be only about 4 units beyond the distal end of the sheath 112 (based upon the position shown of the needle-attached handle member 104). A stylet 110 extends through a lumen of the needle 120 and has a stylet cap 111 fixed on its proximal end. It should be appreciated that other embodiments of the handle described herein, as well as other handle designs appropriate for use in operating a biopsy needle may be practiced within the scope of the present invention.

FIG. 1 includes a detail call-out showing the distal portion of the needle device 100. The needle 120 extends distally beyond the distal end 129 of the sheath 112. As is described below in greater detail, the needle 120 includes two sections—a proximal portion 122, and a distal portion 124. The stylet 110 is shown extending from the distal end of the needle distal portion 124. The stylet 110 is shown as a round-tipped stylet, but it should be appreciated that other stylet designs, including a stylet having a distal end tip beveled or otherwise shaped to match or otherwise complement a distal tip shape and/or geometry of the needle 120.

Figure 1A:
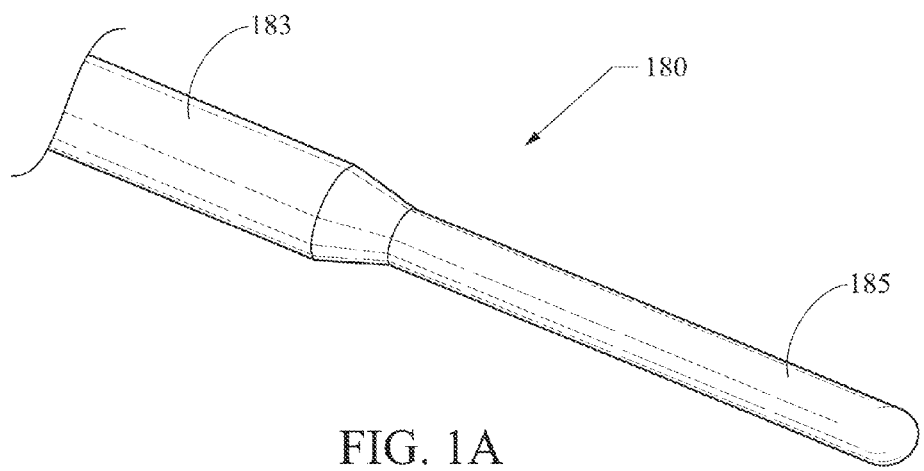
FIGS. 1A and 1B show stylet embodiments with portions including smaller outer diameter.

FIG. 1A shows a stylet embodiment 180 configured to provide or enhance distal flexibility of a needle that the stylet is supporting. The elongate shaft body of the stylet 180 has a first outer diameter portion 183 that may have about the same or slightly smaller diameter than the inner diameter of a needle lumen, in the manner typical of needle stylets in the art. A distal end portion 185 of the stylet body 180 may include a reduced diameter (compared to the larger outer diameter portion 183) that will still provide support for the needle, but that will provide reduced stiffness and improved navigability through, for example, an endoscope working lumen.

Figure 1B:
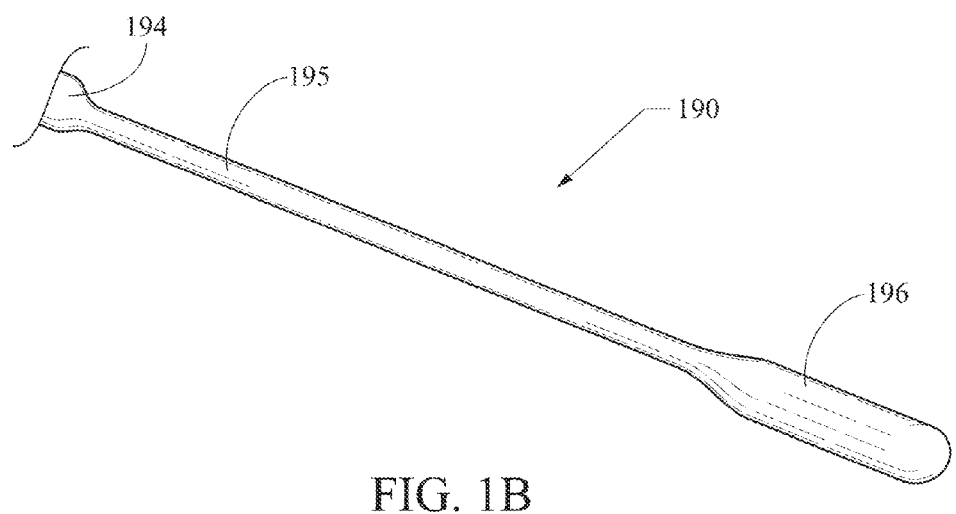

FIG. 1B shows a stylet embodiment 190 configured to provide or enhance distal flexibility of a needle that the stylet is supporting. The elongate shaft body of the stylet 190 has a first larger-outer-diameter ("OD") portion 194 and a second larger-OD portion 196 that each may have about the same or slightly smaller diameter than the inner diameter of a needle lumen, in the manner typical of needle stylets in the art. A distal end intermediate length 195 of the stylet body 190 is disposed between the first and second larger-OD portions 194, 196. The intermediate length 195 includes a reduced diameter (i.e., smaller than one or both of the first and second larger-OD portions 194, 196) that will still provide support for the needle, but that will provide reduced stiffness and improved navigability through, for example, an endoscope working lumen. The first larger-OD portion 194 and the second larger-OD portion 196 each will have a larger outer diameter than the intermediate portion 195, but may have the same or different outer diameters relative to each other.

Figure 2A:
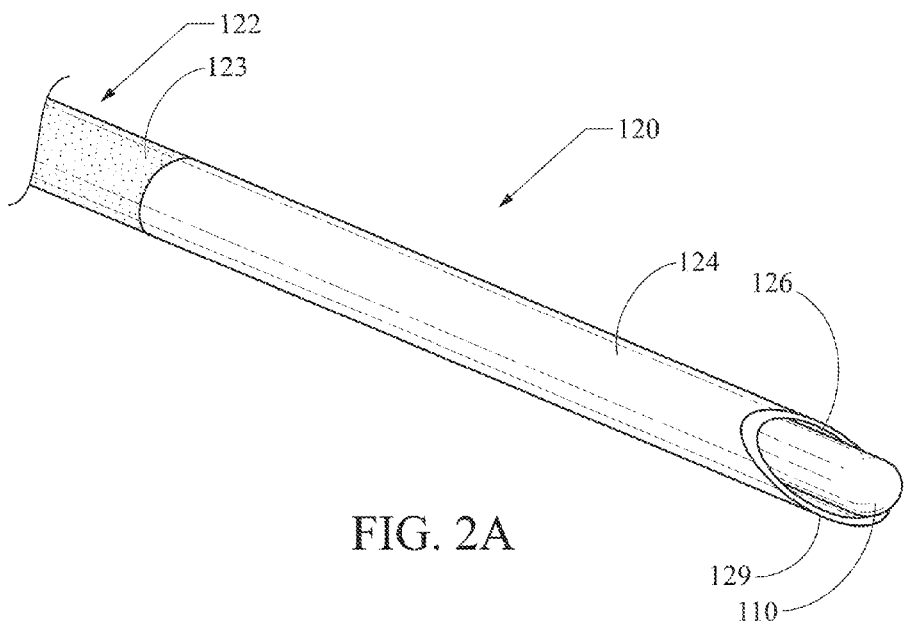
FIGS. 2A and 2B each show a detail view of a distal region of the needle of FIG. 1.
Figure 2B:
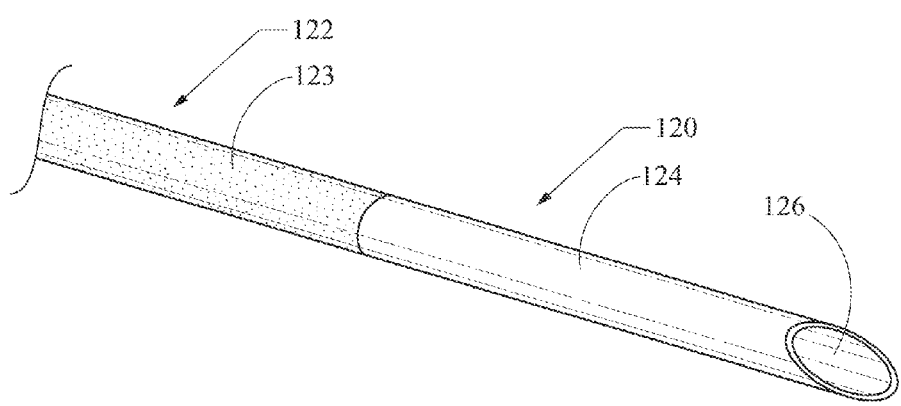

FIGS. 2A and 2B show more detailed perspective views of the needle 120 with, and without a stylet 110, respectively. Certain embodiments configured for use with a stylet 110 may be configured with greater flexibility, as the stylet can be used to provide desirable stiffness, pushability, and trackability when navigating the needle to a target site in a patient body. The distal needle portion 124 includes a distal tip 129, which is shown as a beveled needle tip. It should be appreciated that the distal tip 129 preferably is configured for collecting a tissue sample (e.g., suitable for cytological and/or histological analysis), and may be configured in a variety of ways including with different penetrating needle tip styles known or developed in the art including, for example, Chiba, Franseen, Menghini, Turner, and/or other needle tip types, or it may be constructed as an atraumatic tip (e.g., as in the Cook® ECHO-19-A device). The needle shown includes a needle lumen 126 through which the stylet 110 is disposed in FIG. 2A.

The distal needle portion 124 will generally be much shorter than the proximal needle portion 122. The distal needle portion 124 will preferably be about 20 mm to about 100 mm in length, with one embodiment being at least about 80 mm in length, while the total length of the needle 120 preferably will be configured to access a target site in a patient site via an endoscope (e.g., about 100 cm to about 180 cm, exclusive of a handle) whereby, a combined length of the proximal shaft portion and the distal shaft portion may be configured to access tissue via passage through at least a patient esophagus and stomach. Preferred needle designs will include echogenicity-enhancing features such as, for example, surface dimples, laser etching, grit-blasting, or other structures configured to provide desirable ability to visualize the needle under ultrasound, including endoscopic ultrasound.

It should be appreciated that the proximal needle portion 122 may include a polymer coating 123, as shown in FIGS. 1-2B. FIG. 2C shows a distal region of the needle 120, including a view of a length of the proximal needle portion 122 with the polymer coating 123 removed. The proximal needle portion 122 includes a tubular core 121 that preferably is constructed of the same material as, but with a smaller outer diameter than, the distal needle portion 124. For example, the proximal needle portion core 121 may be configured as a 22-gauge shaft, while the distal needle portion 124 may be configured as a 19-gauge shaft. In certain embodiments, the proximal shaft core portion 121 will measure not larger than about 22 gauge, and the distal shaft portion 124 will measure no less than about 19 gauge.

This construction provides advantageous features for a biopsy needle, including providing a more flexible shaft while still providing a large distal end portion configured for obtaining a sample of desirable size. The "stepped" construction provides for manufacturing efficiency by allowing use of two different sizes of components (i.e., smaller OD shaft tube and larger OD distal needle portion) rather than beginning with a typical single diameter shaft and then augmenting or reducing a portion of its diameter.

Figure 2C:
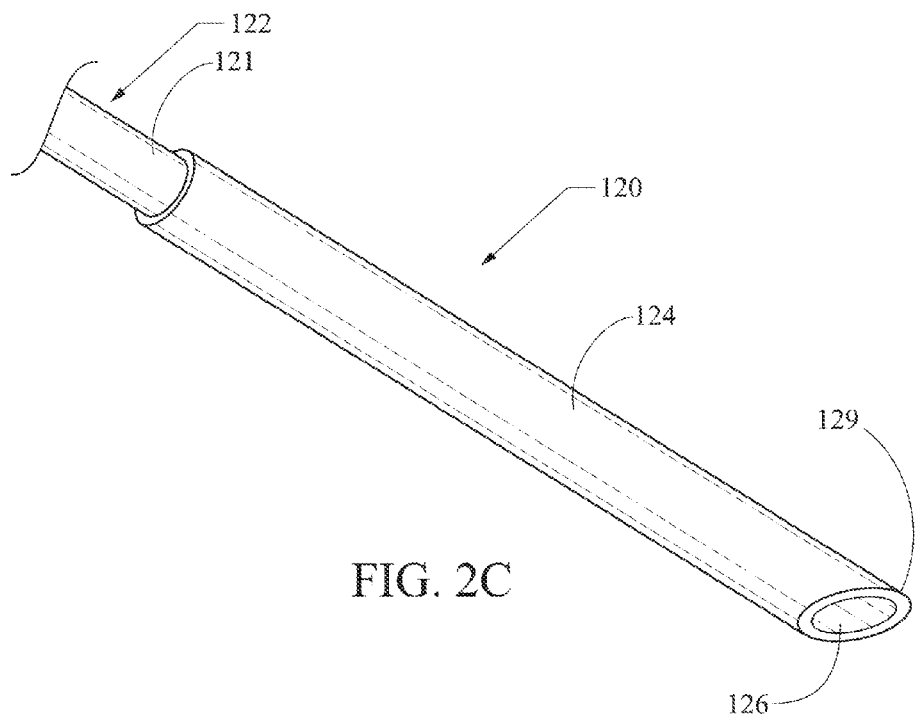
FIG. 2C shows a detail view of a distal region of the needle of FIG. 1, with a polymer coating of a proximal needle shaft portion removed/absent.
Figure 2D:
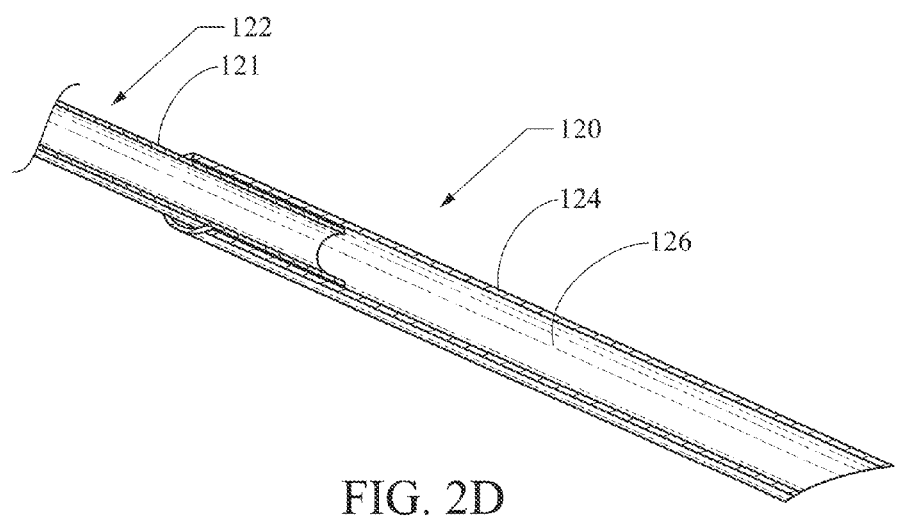
FIG. 2D is a longitudinal section view of FIG. 2C.

FIG. 2D shows a longitudinal section view of FIG. 2C. The proximal needle core portion 121 extends into a joint region of the distal needle portion 124. The proximal and distal needle portions 121, 124 may be joined by any appropriate means known in the art for the materials of which the needle 120 is constructed. For example, the proximal and/or distal needle portions 121, 124 may be constructed of one or more metal alloys (e.g., stainless steel tubing, stainless steel flat wire coil, nitinol, or other alloys appropriate for use in medical biopsy needles), which may be joined by welding, soldering, crimping, annealing, adhesive, or other appropriate joining means. In other embodiments, the needle portions 121, 124 may be constructed of a polymer (e.g., PEEK, PEBAX). The polymeric coating may include PVC, polyethylene, PTFE, and/or other appropriate polymers.

This construction of a smaller diameter proximal shaft core 121 with an overlaying polymer coating 123 will provide desirable pushability and trackability similar to an all-metal shaft or thinly-coated shaft of the type known in the art. However, it will not include the stiffness and challenges of navigation associated with those other devices. At the same time, it retains the advantage of including a larger sample-gathering distal tip region.

Figure 3A:
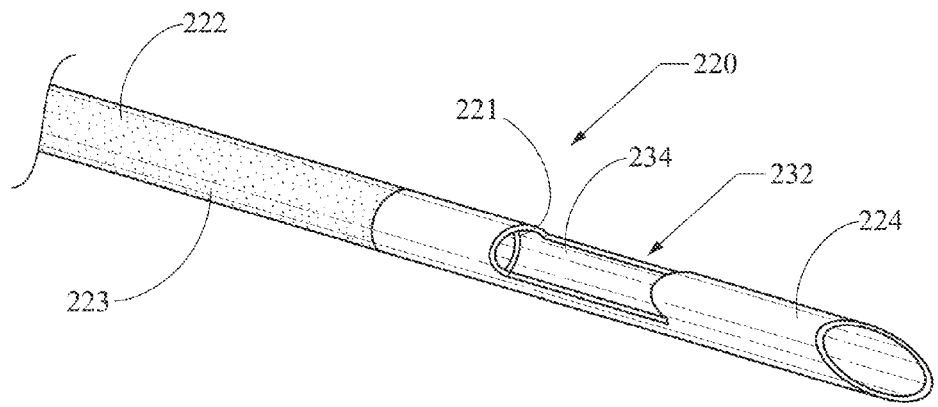
FIGS. 3A and 3B show a notched/apertured embodiment of a needle.
Figure 3B:
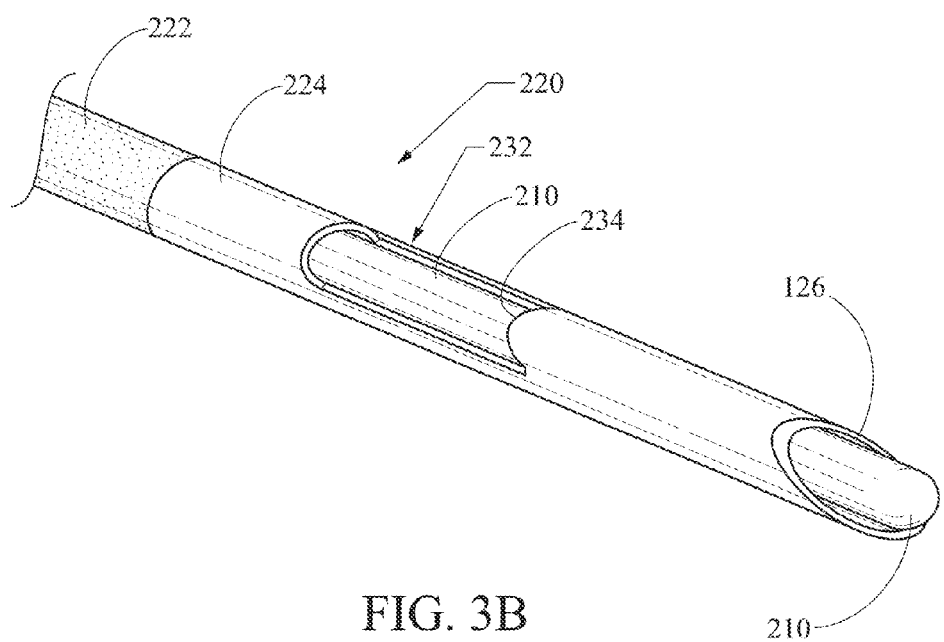

As shown in FIGS. 3A and 3B, a needle 220 may be provided with a proximal portion 222 and a distal portion 224, the distal needle portion 224 includes a side aperture that may be configured as a notch 232. The notch 232 may include a cutting edge 234 that is configured to excise (e.g., cut and/or scrape) tissue for collection of histological and/or cytological samples. The cutting edge 234 is shown in FIG. 3A as facing proximally, but it is known in the art to orient such cutting edges toward the distal end so that distally-directed motion will actuate them, and/or to orient them laterally such that they may be actuated by sideways or rotary motion relative to the longitudinal axis of the needle. These and other aperture cutting edge embodiments may be practiced within the scope of the present invention.

As shown in FIG. 3B, the notched needle 220 may also be used with a stylet 210. The needle 220 of FIGS. 3A-3B includes a polymer coating 223 on its proximal portion 222, while its distal needle portion 224 does not have the polymer coating. In FIG. 3A, the distal end of the proximal shaft portion core 221 in the lumen 226 of the distal shaft portion 224 is visible through the notch 232.

Figure 4:
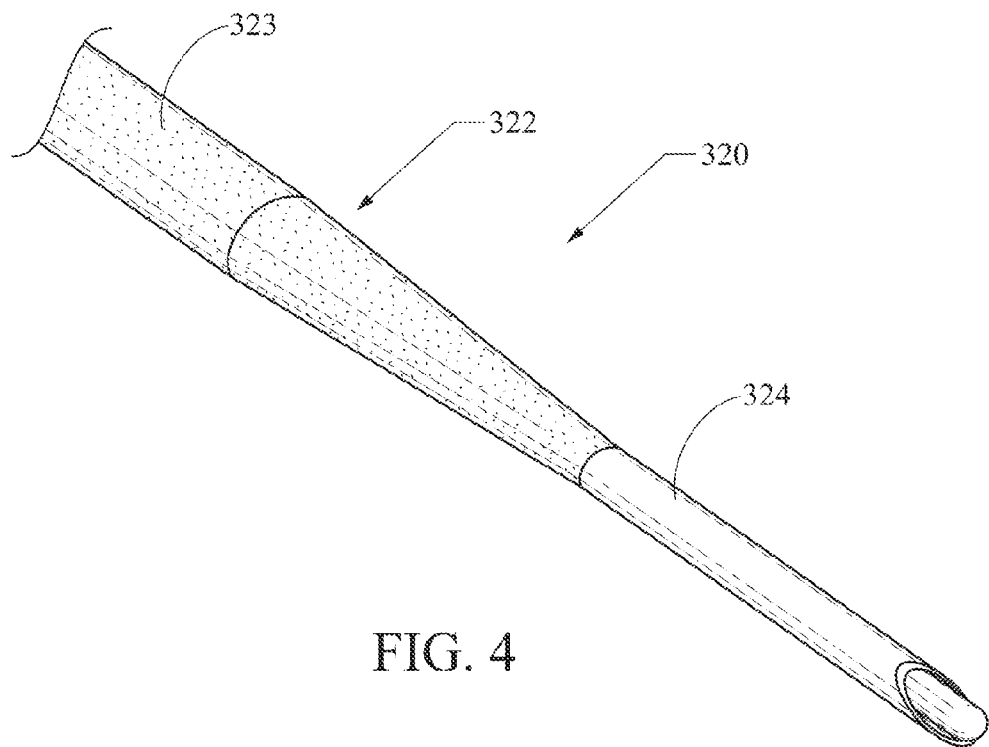
FIG. 4 shows a needle having a larger diameter proximal polymer coating tapering to an outer diameter of a distal needle shaft portion.

As shown in FIGS. 1-2B, the polymer coating 123 of the proximal needle portion 122 may have an outer diameter the same as, very similar, or substantially similar to the outer diameter of the distal needle portion 124 where they meet. However, as shown in FIG. 4, a proximal length of the coated proximal needle portion 322 of a needle 320 may include an outer diameter that is greater than the outer diameter of the distal needle portion 324. That is, the polymeric coating 323 may be constructed such that a length of the proximal needle portion 322 is radially larger than the distal needle portion 324, and—as shown in FIG. 4, the polymeric coating 323 tapers down to match exactly or very nearly the outer diameter of the distal needle portion 324 where they join. The larger diameter proximal body portion of this embodiment will not pose the stiffness and navigation difficulties of a geometrically similar all-metal needle, because—in this embodiment—it will be most preferable to use a polymer coating 323 that is much more flexible than would be possible to obtain with a metal shaft of the same or even slightly smaller diameter. However, providing a smaller-diameter proximal core shaft (not visible, but similar to the core 121 in FIGS. 2C-2D) made of metal or of a stiffer polymer will provide desirable trackability and pushability. In embodiments where the shaft portion is larger in diameter than the needle portion, it is anticipated that only the smaller diameter needle portion may be used to penetrate patient tissue (such as, for example, gastrointestinal submucosa accessed via endoscope where much of the device length remains in a working channel of the endoscope).

Figure 5:
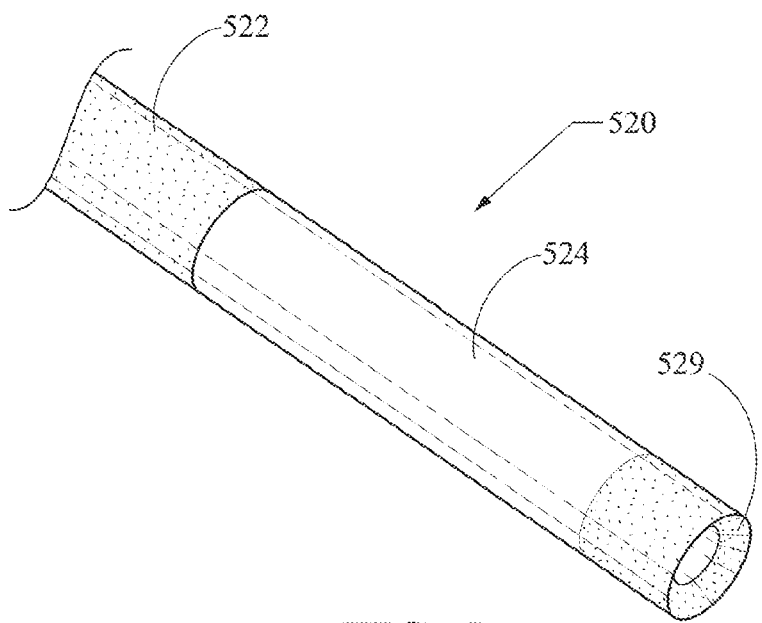
FIG. 5 shows a titanium nitride-coated needle embodiment.

In the embodiment shown in FIG. 5, the distal shaft portion 524 includes a titanium nitride-coated distal cutting tip 529. That is, FIG. 5 illustrates another embodiment of a needle 520, including the "stepped" construction described above, but with a non-beveled distal tip end 529. When using a bevel-tipped needle, the target tissue may sometimes be deflected around the distal lumen opening, resulting in what physicians refer to as a "dry tap," where no sample is obtained. This creates several potential problems: very often the patient must endure another invasive and painful penetrating procedure, and additional time is consumed (and expense created) by the personnel and facilities to repeat the attempt to procure a biopsy. If the guidance is under fluoroscopy, the patient and attending personnel are both subject to increased radiation exposure during the repeated attempt to procure a sample. For body locations and tissue types where there is a known risk of a "dry tap" with a beveled needle, it would be advantageous to provide an endoscopic core biopsy needle that is visualizable under ultrasound and that is configured to minimize the likelihood of a "dry tap."

Titanium nitride is an extremely hard ceramic material that is used as a coating on sewing needles, drill bits, milling cutters, and hole punches to improve edge retention and corrosion resistance. A thin coating of titanium nitride can be applied to a defined area by plasma vapor deposition. Thereafter, the coated region can be ground to a sharp edge to form the titanium nitride-coated needle distal tip 529 shown. As in the embodiments described above, this embodiment is shown with a proximal needle shaft portion 522 that includes a smaller diameter core shaft (not shown) and a larger diameter distal needle shaft portion 524.

The distal tip 529 includes a generally circular (that is, exactly circular, nearly circular, oval, elliptical, or the like) end geometry. The tip 529 is shown as non-beveled—that is, with its distal generally circular cutting end face/tip 529 being substantially perpendicular to the long axis of the distal shaft portion 524. Although it is described here as being advantageous for use with a non-beveled needle-tip design, it should be appreciated that various beveled and other needle designs (e.g., Westcott, Chiba, Franseen, Menghini) may also be constructed with a titanium nitride coating, and practiced within the scope of the present invention.

Figure 6:
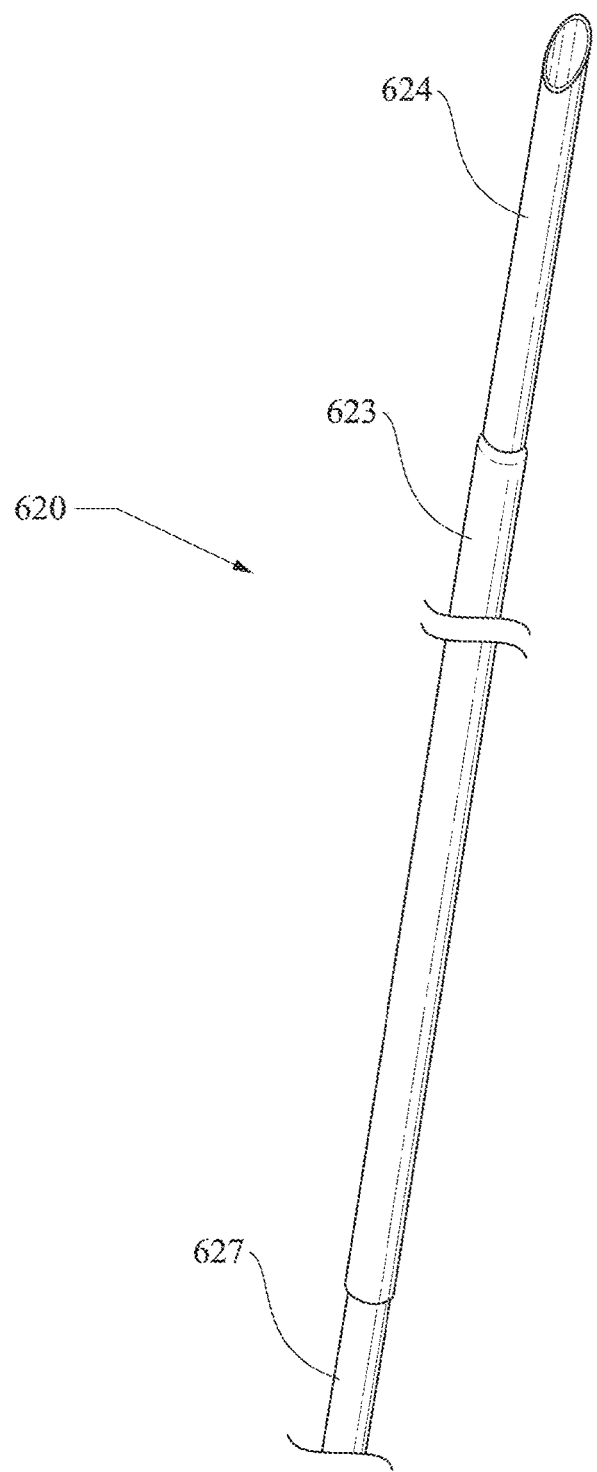

FIG. 6 shows shaft portion 620 of an embodiment of a needle device (the entire device of which may look generally like the needle device 100 of FIG. 1). The shaft portion 620 includes a proximal region 627, an intermediate region 623, and a distal region 624. The distal region 624 is constructed from a metallic material (e.g., stainless steel) that may be configured as a sharp penetrating tip such as, for example, a Franseen, Menghini, or lancet tip, or that may be configured as an atraumatic tip, and preferably will be configured for ultrasound/echogenic visualization by dimpling or another method/structure. The intermediate region 623 is constructed as a flexible polymer tubing that preferably will be constructed in a manner known in the art to provide pushability while including greater flexibility than hypotube or other metallic tubing construction. Those of skill in the art will appreciate that suitable polymers may include PEEK, nylon, and/or combination polymers such as—for example—braided or co-extruded polymers.

Some users of endoscopic needles with metallic shaft bodies have observed that they may be difficult to advance fully into/through an EUS endoscope. The polymer intermediate region 623 may obviate this by providing a shaft with good pushability that will include greater flexibility than metallic shafts of similar gauge, thereby decreasing potential binding in the endoscope working channel. For example, the polymer section 623 may include stiffness, pushability, and/or trackability comparable to a 25 ga stainless steel endoscopy needle, while providing a different inner and outer diameter along that section, with—for example—a 19 ga distal needle end for interacting with tissue. This difference in inner diameter may provide for increased ability to direct fluid or apply suction through the needle, while the difference in outer diameter may provide for desirable directability through an endoscope working channel.

The proximal region 627 may be constructed of metallic tubing in the manner of existing endoscopic needles, the same or a different polymer than the intermediate region 623, and/or a coated metallic tubing. The outer diameter of the intermediate region 623 may be the same, greater than, or less than the outer diameters of the proximal region 627 and the distal region 624, which may be the same or different than each other. An embodiment with this polymer-only intermediate portion may provide a proximal portion with greater rigidity, an intermediate portion with greater flexibility (than either end portion) while retaining desirable pushability, and a distal end needle portion configured to penetrate or otherwise interact with a target region accessible via an endoscope. The enhanced flexibility of the intermediate portion over current devices may provide advantages in accessing anatomical locations that are not readily accessible to less flexible metal-body cannulas used in many current endoscopic echogenic needle devices.

The length of a "polymer-only" intermediate region 623 may be relatively short or long in comparison to the overall needle length. For example, in a gastrointestinal endoscopy needle of about 180 to about 320 cm in length, the polymer section may be only about 40 to about 320 mm in length, although the length may be greater or less. For example, in one embodiment of a needle, the intermediate polymer section of a 240 cm needle device is only about 180 mm in length, with a distal metal needle end that is 26 mm in length. However, the distal metal needle length may be less than about 10 mm, such as, for example, about 4 mm. This generally distal location of the enhanced-flexibility polymeric device length may provide desirable flexibility along the portion most likely to be directed through restricted, tortuous, or otherwise difficult-to-navigate paths (e.g., in and/or exiting an endoscope working lumen, in a patient body lumen, extending through body tissue). In one example/embodiment, a combined length of the proximal shaft portion and the distal shaft portion may be configured to access tissue via passage through at least a patient esophagus and stomach. In these and other embodiments, larger-outer-diameter shaft lengths may be located/configured where they will not penetrate tissue, but will remain in an endoscope working lumen or open body lumen.

Figure 6A:
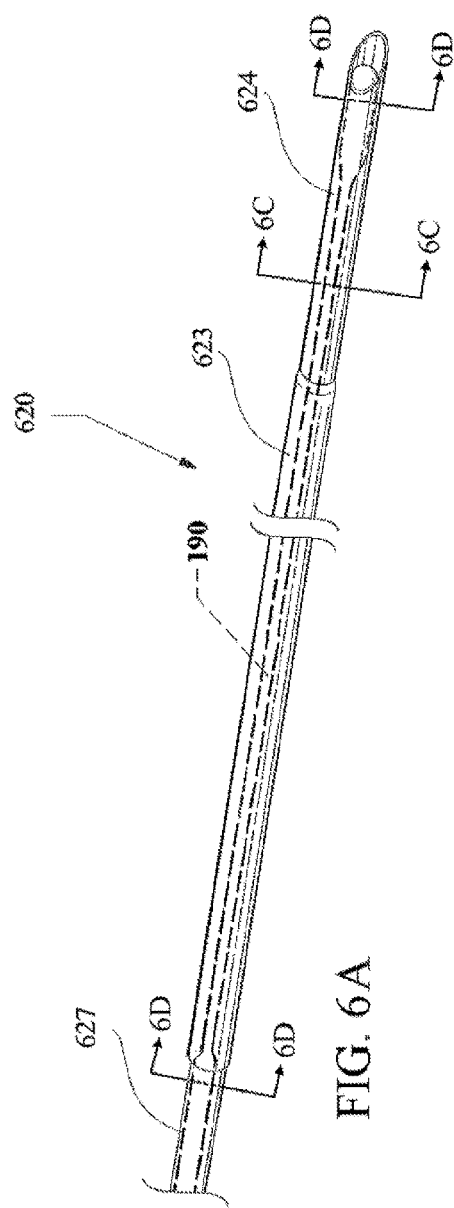
FIG. 6A shows that needle embodiment with a stylet.
Figure 6B:
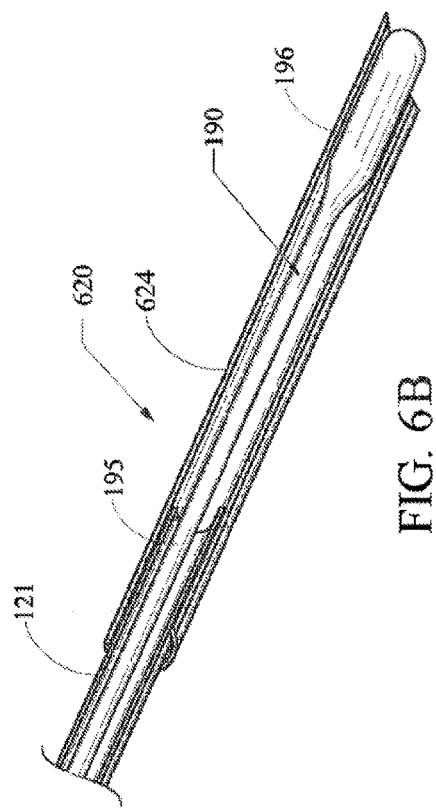
FIG. 6B shows a distal detail view thereof (excluding the polymeric portion for purposes of illustrative clarity/simplicity) with the outer needle structure shown in longitudinal cross-section.
Figure 6C:
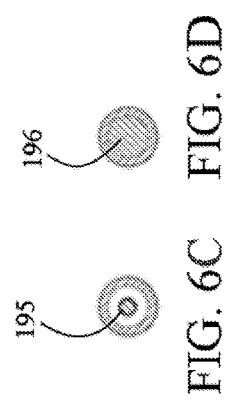
FIG. 6C shows the relative size and orientation of a smaller-diameter stylet portion in a transverse cross-sectional view at reference arrow 190 of FIG. 6B.
Figure 6D:
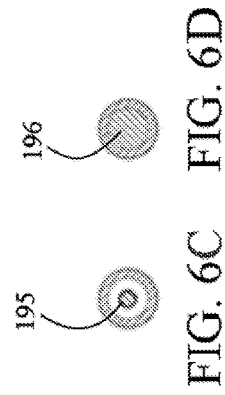
FIG. 6D shows the relative size and orientation of a larger-diameter stylet portion in a transverse cross-sectional view at reference line 196 of FIG. 6B.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle embodiment may be provided including and combining features described with reference to the drawing figures, such as—by way of non-limiting illustration—a needle with a distal metal portion as shown in FIGS. 2C-2D, where the smaller-diameter tubular core 121/221 can be covered with a consistent outer diameter polymer as shown in FIGS. 2A-2B/3A-3B, or with a tapered polymer exterior as shown in FIG. 4, with or without a notch (FIGS. 3A-3B), and with an intermediate length (immediately adjacent and proximal of the distal metal portion with its tubular core 121) being "polymer-only," and a metallic proximal region 627 that is immediately adjacent and proximal of the intermediate polymer-only length, as shown in FIG. 6, where a stylet used therein may be embodied as shown in FIG. 1A or FIG. 1B. As such, one skilled in the art will appreciate that an exemplary embodiment may include a needle (shown generally in FIG. 6 with reference to an overall assembly shown in FIG. 1), with a lumen through which the stylet of FIG. 1B is disposed, with a proximal metallic portion 627 immediately adjacent an intermediate polymer-only length 623, where the polymer-only length 623 has an outer diameter greater than the proximal metal portion 627, where the polymer-only length 623 tapers down to about the same outer diameter as a distal metallic needle portion 124/324/624 in the manner shown in FIG. 4, where the tapering portion of polymeric material covers/coats a metallic inner tubular core 121 (see FIGS. 2C-2D and FIG. 4 with corresponding text), which will be understood with reference only to the figures and text above, but which may further be clarified with reference to a tabular description as set forth below, and to FIGS. 6A-6D, where FIG. 6A shows the shaft portion 620 of FIG. 6, with a phantom-line representation of a stylet embodiment 190 according to FIG. 1B may be disposed therein, and FIG. 6B shows a partial-section view of a distal end portion of the shaft 620 without the polymeric material but with the stylet 190 disposed through its lumen with FIGS. 6C and 6D respectively showing the smaller-outer diameter and larger-outer-diameter portions 195, 196 of the stylet 190 in transverse section:

| to Proximal End ← | metallic tube length 627 | intermediate non-metallic polymer-only material length 623 | distal shaft portion 323 121 124/324/624 | to Distal End → |
|---|---|---|---|---|
| | | "proximal shaft portion" "immediately adjacent" elements endoscopic tissue-sampling needle | | |

It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. An endoscopic tissue-sampling needle, comprising:
an elongate tubular needle shaft having a proximal shaft portion and a distal shaft portion, said elongate tubular needle shaft including sufficient length and flexibility to extend through and operate outside a distal end of at least one of an end-viewing gastric endoscope, duodenoscope, or endoscopic ultrasound endoscope;
wherein the distal shaft portion comprises a shorter length than the proximal shaft portion;
wherein a length of the proximal shaft portion comprises a non-metallic polymeric material length disposed immediately proximally adjacent of and securely fixed to the distal shaft portion, said non-metallic polymeric material length comprising a greater flexibility than the distal shaft portion;
wherein the distal shaft portion
comprises a metallic material; and
is configured for collection of patient tissue;
the proximal shaft portion further comprising a metallic tube length disposed immediately proximally adjacent of and securely fixed to the non-metallic polymeric material length, separating the non-metallic polymeric material length distally apart from a handle member;
wherein the elongate tubular needle shaft is configured and dimensioned for passage through a working channel of the at least one of the end-viewing gastric endoscope, duodenoscope, or endoscopic ultrasound endoscope to a target site within a patient body;
wherein the non-metallic polymeric material length comprises a first length with a substantially uniform first outer diameter that is larger than an outer diameter of the distal shaft portion, which first outer diameter tapers proximally-to-distally along a transition length and said transition length ends at a second outer diameter that is about the same as the outer diameter of the distal shaft portion, which outer diameter of the distal shaft portion is substantially uniform along an entire length of the distal shaft portion;
wherein the proximal shaft portion includes a proximal shaft lumen, the distal shaft portion includes a distal shaft lumen, and the proximal and distal shaft lumens together provide a continuous shaft lumen;
further comprising a stylet;
wherein the stylet comprises a proximal length having a first outer diameter, a single intermediate length of a second outer diameter that is less than the first outer diameter of the stylet and provides a single gapped void space that continuously and fully extends circumferentially around and longitudinally between the second diameter of the single intermediate length and an inner surface of the continuous shaft lumen, and a distal length having a third outer diameter that is greater than the second outer diameter of the stylet;
wherein the single intermediate length of the stylet is disposed distal of the proximal length of the stylet, and the distal length of the stylet is disposed distal of the single intermediate length of the stylet;
wherein the single intermediate length of the stylet is a greater length than the distal length of the stylet;
wherein the stylet is disposed through at least a portion of the continuous shaft lumen; and
wherein the proximal shaft portion further comprises a proximal core shaft portion that is disposed between the distal shaft portion and the metallic tube length and that the non-metallic polymeric material length coaxially surrounds.

2. The needle of claim 1, further comprising at least one surface feature disposed on the elongate tubular needle and configured to enhance echogenicity.

3. The needle of claim 1, further comprising a tissue-penetrating distal end tip disposed at a distal end of the distal shaft portion.

4. The needle of claim 1, wherein the distal shaft portion comprises a notched aperture in at least one side.

5. The needle of claim 4, wherein the notched aperture comprises at least one cutting edge configured to enhance the collection of the patient tissue from the patient body.

6. The needle of claim 1, wherein the distal shaft portion is about 20 mm to about 100 mm in length.

7. The needle of claim 1, wherein the proximal shaft core portion measures not larger than about 22 gauge, and the distal shaft portion measures no less than about 19 gauge.

8. The needle of claim 1, wherein the proximal shaft core portion measures about 22 gauge, and the distal shaft portion measures about 19 gauge.

9. The needle of claim 1, wherein a distal cutting tip of the distal shaft portion comprises a titanium nitride coating.

10. The needle of claim 9, wherein the distal cutting tip comprises a generally circular, non-beveled cross-sectional geometry.

11. The needle of claim 1, wherein a combined length of the proximal shaft portion and the distal shaft portion is configured to access said patient tissue via passage through at least a patient esophagus and stomach.

12. A method of obtaining a biopsy sample with an endoscopic tissue-sampling needle, the method comprising:
providing an elongate tubular needle shaft of the tissue-sampling needle having a proximal shaft portion and a distal shaft portion, said elongate tubular needle shaft including sufficient length and flexibility to extend through and operate outside a distal end of an end-viewing gastric endoscope, duodenoscope, or endoscopic ultrasound endoscope;
wherein the distal shaft portion comprises a shorter length than the proximal shaft portion;
wherein a length of the proximal shaft portion comprises a non-metallic polymeric material length disposed immediately proximally adjacent of and securely fixed to the distal shaft portion, said non-metallic polymeric material length comprising a greater flexibility than the distal shaft portion;
wherein the distal shaft portion comprises a metallic material and is configured for collection of patient tissue;
wherein the proximal shaft portion further comprises a metallic tube length disposed immediately proximally adjacent of and securely fixed to the non-metallic polymeric material length, separating the non-metallic polymeric material length distally apart from a handle member;
wherein the non-metallic polymeric material length comprises a first length with a substantially uniform first outer diameter that is larger than an outer diameter of the distal shaft portion, which first outer diameter tapers proximally-to-distally along a transition length and said transition length ends at a second outer diameter that is about the same as the outer diameter of the distal shaft portion, which outer diameter of the distal shaft portion is substantially uniform along an entire length of the distal shaft portion;

wherein the proximal shaft portion includes a proximal shaft lumen, the distal shaft portion includes a distal shaft lumen, and the proximal and distal shaft lumens together provide a continuous shaft lumen;

further providing a stylet for providing desirable stiffness, pushability, and trackability when navigating the elongate tubular needle shaft to a target site in a patient body, wherein the stylet comprises a proximal length having a first outer diameter, a single intermediate length of a second outer diameter that is less than the first outer diameter of the stylet and provides a single gapped void space that continuously and fully extends circumferentially around and longitudinally between the single intermediate length and an inner surface of the continuous shaft lumen, and a distal length having a third outer diameter that is greater than the second outer diameter of the stylet;

wherein the single intermediate length of the stylet is disposed distal of the proximal length of the stylet, and the distal length of the stylet is disposed distal of the single intermediate length of the stylet;

wherein the single intermediate length of the stylet is a greater length than the distal length of the stylet;

wherein the stylet is disposed through at least a portion of the continuous shaft lumen;

wherein the proximal shaft portion further comprises a proximal core shaft portion
    that is disposed between the distal shaft portion and the metallic tube length,
    that the non-metallic polymeric material length coaxially surrounds, and
    that the single intermediate length of a second outer diameter is disposed within;

wherein an axis along the single intermediate length of the second outer diameter of the stylet is coaxial with an axis along the non-metallic polymeric material length;

passing the elongate tubular needle shaft and stylet through a working channel of the end-viewing gastric endoscope, duodenoscope, or endoscopic ultrasound endoscope to said target site, and excising the patient tissue from the target site using the distal shaft portion of the elongate tubular needle shaft.

\* \* \* \* \*